United States Patent [19]
Pflugrath et al.

[11] Patent Number: 5,603,323
[45] Date of Patent: Feb. 18, 1997

[54] MEDICAL ULTRASONIC DIAGNOSTIC SYSTEM WITH UPGRADEABLE TRANSDUCER PROBES AND OTHER FEATURES

[75] Inventors: Lauren S. Pflugrath, Seattle; Jacques Souquet, Issaquah, both of Wash.

[73] Assignee: Advanced Technology Laboratories, Inc., Bothell, Wash.

[21] Appl. No.: 607,894

[22] Filed: Feb. 27, 1996

[51] Int. Cl.$^6$ .................................................... A61B 8/00
[52] U.S. Cl. ..................... 128/660.01; 128/903; 128/904
[58] Field of Search .................... 128/660.01, 660.02, 128/903, 904; 364/413.01, 413.02, 413.13, 413.25

[56] References Cited

U.S. PATENT DOCUMENTS

| | | | |
|---|---|---|---|
| 4,545,251 | 10/1985 | Uchida et al. | 73/631 |
| 4,694,680 | 9/1987 | Tajeycgu et al. | 73/1 DV |
| 4,867,168 | 9/1989 | Stoor et al. | 128/653 |
| 5,230,339 | 7/1993 | Charlebois | 123/660 |
| 5,371,692 | 12/1994 | Draeger et al. | 364/413.01 |
| 5,487,386 | 1/1996 | Wakabayashi et al. | 128/660.01 |
| 5,544,651 | 8/1996 | Wilk | 128/660.02 |

OTHER PUBLICATIONS

"Remote diagnostics can cut costs and downtime", G. Freiherr, *Diagnostic Imaging*, Feb. 1996.

*Primary Examiner*—George Manuel
*Attorney, Agent, or Firm*—W. Brinton Yorks, Jr.

[57] ABSTRACT

A remotely upgradeable medical diagnostic ultrasound system is described which is upgradeable with a new transducer probe by means of air shipment of the upgrade hardware and remote transmission of upgrade data which controls operation of the probe. The ultrasound system includes a data communicator such as a network link or modem for receiving upgrade data from a remote location. A process for upgrading the system is provided whereby a communications link is established over a common carrier communications medium between the ultrasound system and a remote terminal, which transmits upgrade program data to the ultrasound system. The program data portion of an upgrade is provided via the communications link while the hardware portion of the upgrade is shipped by air freight to the user. In this way, an ultrasound upgrade can be provided to a user from a remote location in a matter of hours.

37 Claims, 6 Drawing Sheets

MEDICAL ULTRASONIC DIAGNOSTIC SYSTEM WITH UPGRADEABLE TRANSDUCER PROBES AND OTHER FEATURES

This invention relates to medical ultrasonic diagnostic systems and, in particular to medical ultrasonic diagnostic systems which are capable of being remotely upgraded with new transducer probes and other additional performance features.

Early ultrasound machines were built to permanently operate in the specific ways for which they were designed. Generally a system would operate with one or two probes, which might be capable of an A-line scan and audio Doppler for instance. The ability to vary the operating characteristics of the system and probes as extremely limited.

The first advance in system versatility was the development of modular systems. A system such as the Mark III system sold by Advanced Technology Laboratories, Inc. during the 1970's would be assembled from modules, each of which would control a certain aspect of the system operation such as B mode imaging, Doppler processing, or video image formation and display. New features could be added to the system by adding new modules. A user could upgrade the system by buying a new module which would be cable connected to the other modules into a rack of modules to interconnect the modules into a coordinated operating ultrasound system.

As electroncs started to become more compact and integrated, it became possible to consolidate discrete functions and features of an ultrasound system to a single printed circuit board. Ultrasound systems such as the Ultramark 4 system thus could be upgraded with new features and options by replacing existing boards with, or adding, new printed circuit boards.

From circuit board upgrades, succeeding generations of ultrasound systems provided the ability to upgrade through ever smaller components. These systems could be upgraded to operate with new or additional transducer probes by removing existing programmable read-only memories (PROMs) from printed circuit boards and/or plugging new PROMs into the boards. The PROMs were capable of retaining large amounts of digital data, and the sockets for the PROMs provided the pathways, or busses, by which the program data stored in the PROMs could be accessed by the processor of the ultrasound system. A typical transducer probe upgrade by which a new probe would be added to operate on an existing system would include the probe and cable, and one or more PROMs which would provide program data by which the ultrasound system would control and operate the new probe.

These developments have led to the ultrasound systems of today, where portions of some ultrasound system upgrades are installed by service personnel from digital data storage media. In some systems much of the program data is stored on a hard disk drive which can be replaced by a serviceman. An upgrade to new features such as new transducer probes can be performed by removing the ultrasound system's existing disk drive and replacing it with a new disk drive which has been prepared and tested at the factory with new program data. Thus a completely new program data set, which has been prepared and fully tested and verified at the factory, is installed in the ultrasound system to provide the system with the ability to be operated with new or different transducer probes or to perform advanced new functions and features such as three dimensional display processing.

In the most recent evolution of data processing media, the new program data is stored at the factory on a high density medium such as an optical disk. To install new program data for new system features, a serviceman will insert the optical disk into an optical disk reader built into the ultrasound system. The ultrasound system will then be operated to read the new program data from the optical disk and store it on the system's hard disk drive or other data storage devices. A serviceman can thus carry one or a limited number of optical disks for the various ultrasound system models in a product line, and selectively load the needed data from the proper optical disk into each ultrasound system he is repairing or upgrading.

One element that has not changed with these advances is the need for ultrasound system upgrades to be performed by trained and highly skilled ultrasound system service personnel. The ever increasing complexity and sophistication of these machines have seemingly made the installation of upgrades by service personnel an even greater imperative than ever before. While hospital medical technicians at times can possess the requisite skills for such installation, their presence at the site of every ultrasound system cannot be assumed, and medical professionals who use ultrasound systems in their medical practices generally are unfamiliar with system service techniques. It is desirable to be able to upgrade ultrasound systems with new and different transducer probes and other features without the need for personal involvement by service personnel, keeping in mind that on-site support at the ultrasound system location will generally not be available. Furthermore, a physician cannot always wait for the arrival of a serviceman. A physician may need new capabilities or system features for a difficult or unusual diagnosis within a day's time or even a matter of hours. Thus, it is desirable to be able to quickly provide a physician with upgraded features and capabilities for his ultrasound system, even when service personnel are unavailable or cannot be timely scheduled for an upgrade service call.

In accordance with the principles of the present invention, an ultrasonic diagnostic system is provided which is capable of being remotely upgraded with new or different transducer probes, or other performance features. The ultrasound system is equipped with communications electronics such as a modem or network capability, enabling the system to communicate and exchange data with the factory or other location from which new program data is transmitted to the system by telephone line or other communications system. Transducer probes are inventoried at a central geographic location from which they may be quickly air freighted to any ultrasound system location in the region or country. When a physician orders an upgrade feature such as a new transducer probe, the probe is air freighted within hours to the physician from the central inventory location. When the ultrasound system is set by a user to a state in which an upgrade may be installed, the program data necessary for control and operation of the probe by the ultrasound system is electronically sent to the ultrasound system from the factory over a telephone or other communications network. The transmitted data is received by the modem or network link in the ultrasound system, stored, and installed in the system's processing and memory electronics. The ultrasound system performs a verification of the newly installed program data and reports the successful upgrade installation to the factory or other data source. If desired, the user can perform a simple verification of the upgrade feature the next time the ultrasound system is operated, or transmit data to the factory or other service depot when any problems with the upgrade feature can be assessed and resolved. Thus, an ultrasound system upgrade can be performed without the need for service personnel involvement at the ultrasound system site, and with simple and minimal interaction with system users.

Figure 1:
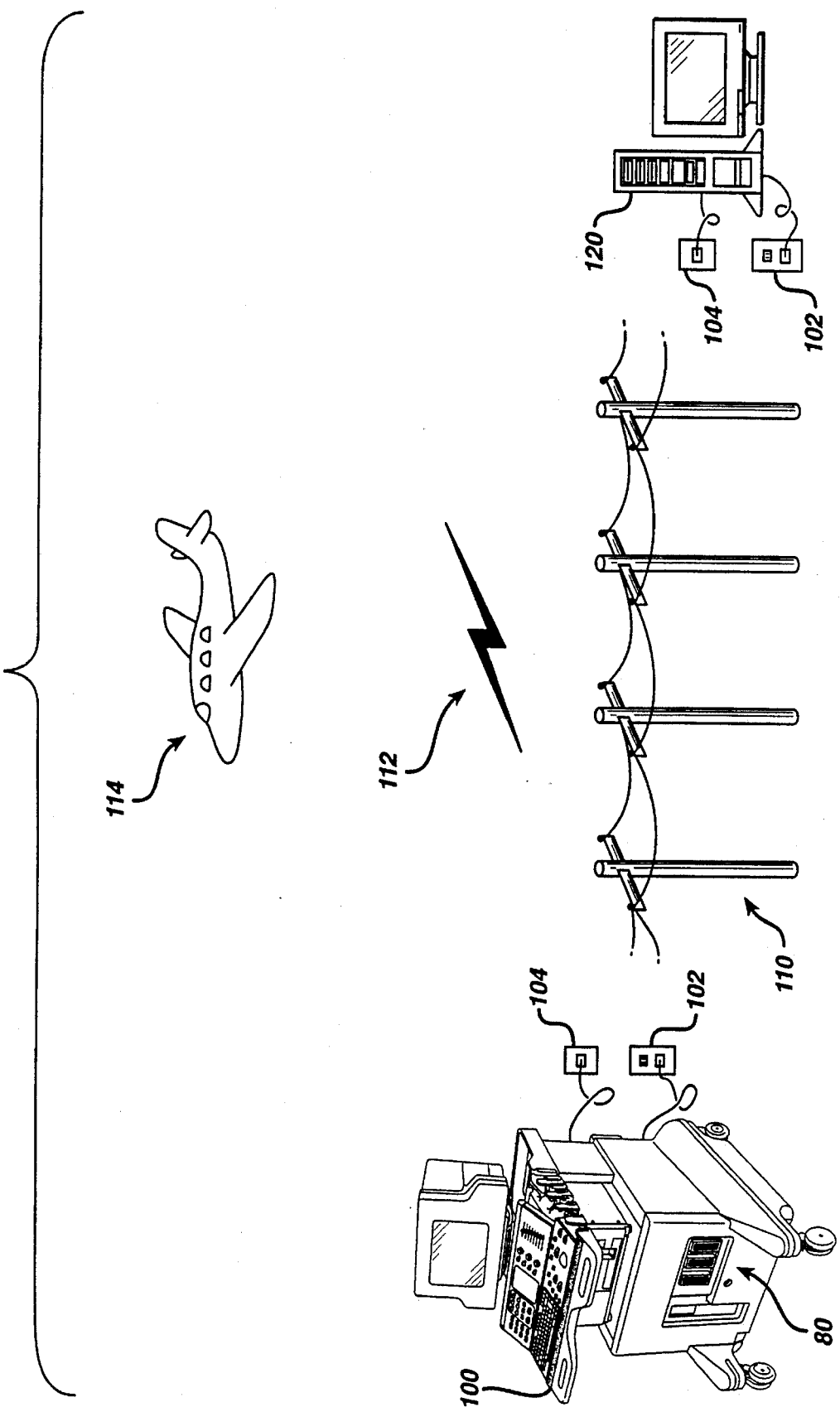
FIG. 1 illustrates the concept of a remotely upgradeable diagnostic ultrasound system in accordance with the present invention.

Referring first to FIG. 1, the concept of a remotely upgradeable diagnostic ultrasound system in accordance with the present invention is shown. As used herein, the term "upgrade" refers to hardware and/or digital data for a medical diagnostic ultrasound system which, when installed in the system, provide the system with features and functions which the system does not presently possess. An example of an upgrade is a new or different model of transducer probe, for instance, or the capability to display ultrasonic images in three dimensional presentation. With the present invention, the conventional need for an on-site visit by service personnel to install upgrades is eliminated, as the hardware and digital data of an upgrade are provided by direct air freight shipment and electronic data communication, respectively.

In FIG. 1, a medical diagnostic ultrasound system 100 is located at a user site such as a hospital, laboratory, or clinic. The ultrasound system 100 is plugged into an a.c. outlet 102 to power the system in the conventional manner. In addition, the ultrasound system is connected to a communications network at connector 104, by which the digital or program data portion of an upgrade can be remotely provided by way of common carrier communications systems such as the telephone network indicated at 110, or by radio, satellite link, or other wireless communication network as indicated at 112, which transmits data between geographically separated locations. Common carrier systems are generally accessible to or used by members of the public. The hardware portion of an ultrasound system upgrade is provided by direct air freight shipment as indicated by the airplane 114, while the data portion of the upgrade is transmitted directly to the user site from an upgrade data server 120. As in the case of the ultrasound system 100 with which the upgrade data server is communicating, the upgrade data server 120 is plugged into a conventional a.c. outlet 102 for electrical power, and connected to communications network connector 104 for the transmission of ultrasound system data upgrades over the communications media 110,112. The term "server" as used herein means a data transmission device which transmits upgrade data for an ultrasound system over a communications medium.

Figure 2:
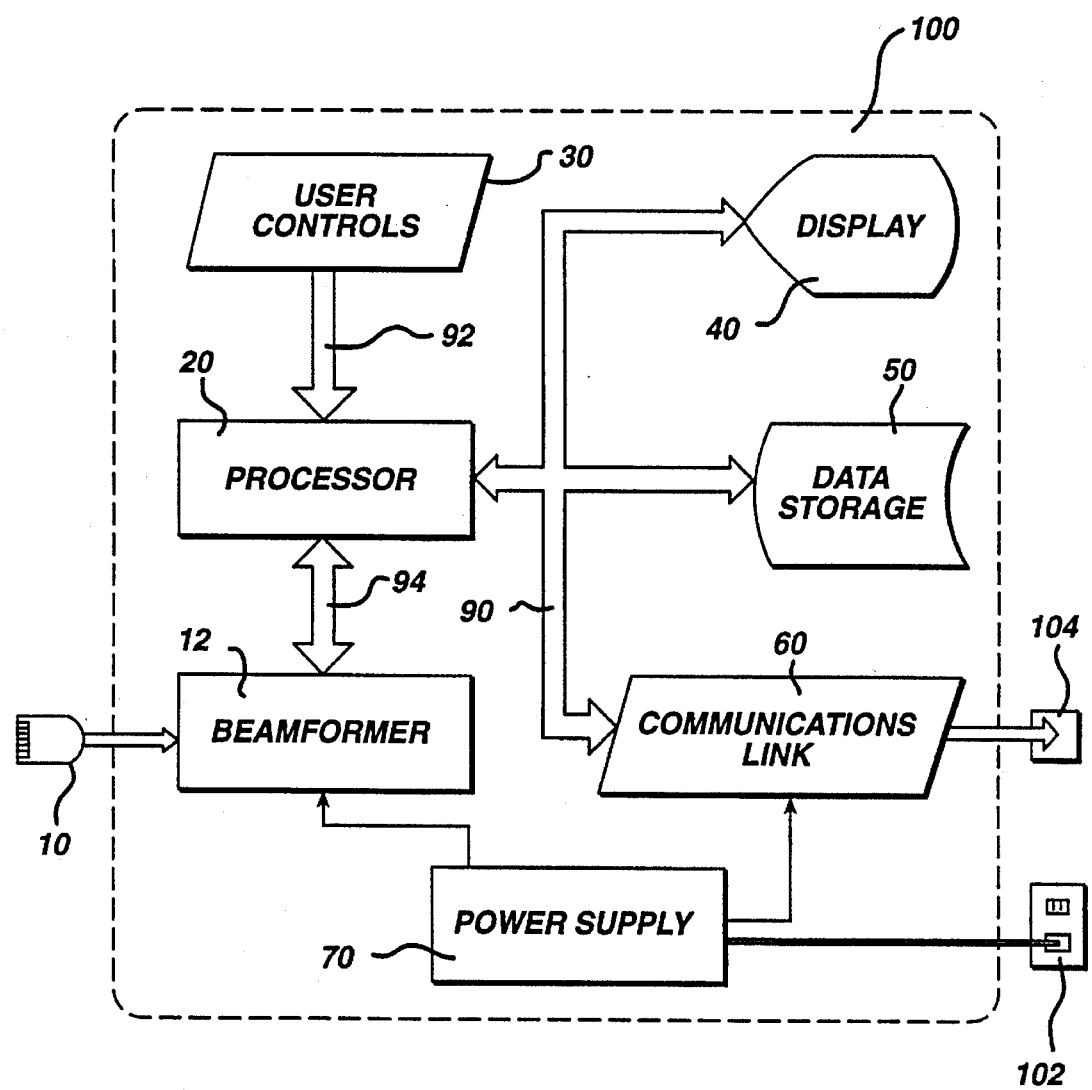
FIG. 2 illustrates in block diagram form major component parts of a remotely upgradable diagnostic ultrasound system constructed in accordance with the principles of the present invention.

A detailed block diagram of the remotely upgradeable ultrasound system 100 is shown in FIG. 2. The dashed block 100 outlines the ultrasound system components which are integrated together on the cart or frame of the ultrasound system. The ultrasound system 100 includes a processor 20 which responds to inputs from user controls 30, processes ultrasonic information, and controls the overall operation of the ultrasound system. Information and commands from the user controls 30 are applied to the processor 20 over a data bus 92. Ultrasonic energy is transmitted into the body of a patient from an ultrasonic transducer probe or scanhead 10, which is connected to a beamformer 12. The ultrasound system 100 normally includes a number of scanhead connectors as shown at 80 in FIG. 1, through which a number of scanheads may be simultaneously connected to the beamformer 12. The beamformer commands a selected scanhead 10 to transmit ultrasonic energy and receives ultrasonic echo information from the scanhead which is processed by the beamformer 12, all under the control of signals provided over a bus 94 from the processor 20. The processor 20 processes the ultrasonic information produced by the beamformer to form display information such as an ultrasonic B mode image, Doppler images or spectral information, or other information derived from the ultrasound information. The display information is routed over a data bus 90 for display on a display monitor 100. The displayed information may also be stored in data storage media 50, which may include image storage arrangements such as a Cineloop® memory. The data storage media also store program data which is accessed over the bus 90 by the processor 20 and used to control various functions of the ultrasound system or process the ultrasound information in unique ways. The program data may include programs for processing ultrasound image data for three dimensional display, for instance, or to simultaneously process and display an ultrasound image and spectral Doppler information, or to control the beamformer or a specific scanhead model, for example.

In accordance with the principles of the present invention, the ultrasound system includes a communications link 60 for communicating with and receiving upgrade program data from the factory of the ultrasound system manufacturer. The term "factory" as used herein refers to a remote location from which ultrasound system program data is transmitted to a user's ultrasound system, and may include the location where the system is manufactured, a service location, a distribution location, or some other location where a server for transmitting program data to the ultrasound system is located. The communications link 60 may take the form of a network interface such as an Ethernet port which communicates through a network in the facility where the ultrasound system resides, or it may take the form of a modem which interfaces to telephone lines. In either case the communications link is capable of communicating with and receiving program data transmitted to the ultrasound system from the factory. The communications link 60 is controlled within the ultrasound system 100 by the processor 20, and program data received by the communications link 60 from the factory may be processed by the processor 20 or stored in the data storage media 50, or both.

The electronic components of the ultrasound system 100 are powered by voltages developed by a power supply 70, which is plugged into an a.c. outlet 102 in the conventional manner.

Figure 3:
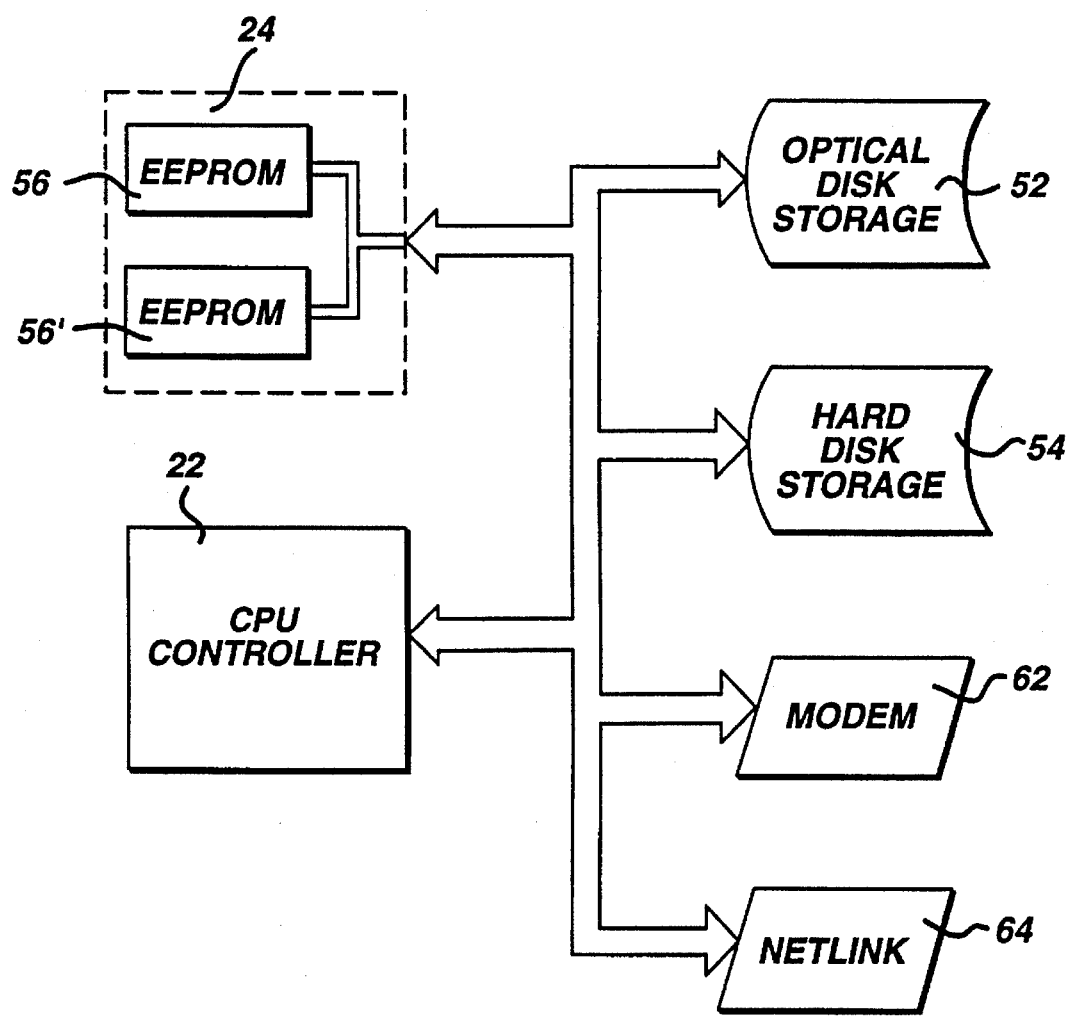
FIG. 3 illustrates in block diagram form an exemplary data storage and control system of a remotely upgradable ultrasound system.

FIG. 3 is a block diagram providing an example of the processor and storage media bus architecture of a remotely upgradeable ultrasound system. Connected to the data bus 90 in this drawing is a central processing unit (CPU) and controller 22, which controls the flow of program data between a modem 62 and a number of storage elements. The communications link is provided in this example by the modem, which is capable of transmitting and receiving program data between the ultrasound system and external data sources. As an alternative, or in addition to, the modem 62, the communications link may comprise a network communicator such as the netlink communicator 64. Netlink communicators for ultrasound systems are available from the present inventors' assignee company, and are capable of communicating with a network in the facility where the ultrasound system is located, which networks may then communicate with external data sources.

The storage elements shown in FIG. 3 include a hard disk storage device 54, an optical disk storage device 52, and a custom processor board 24 on which are located several electrically programmable logic devices such as electrically erasable, programmable read-only memories (EEPROMs). In a typical arrangement the hard disk storage device 54 would store programs and data tables which are recalled and executed or utilized as required by the CPU and controller 22. The optical disk storage device would hold information requiring high density storage, such as ultrasound images. The EEPROMs would hold data which is used in the course of performance of specialized operations or dedicated function by the custom processor 24. The CPU and controller 22 may receive program data from the modem and store it directly in one of these storage elements; it may store received program data temporarily, then process and store the processed information in a storage element; or it may process received program data immediately, then store it in a storage element.

Figure 4A:
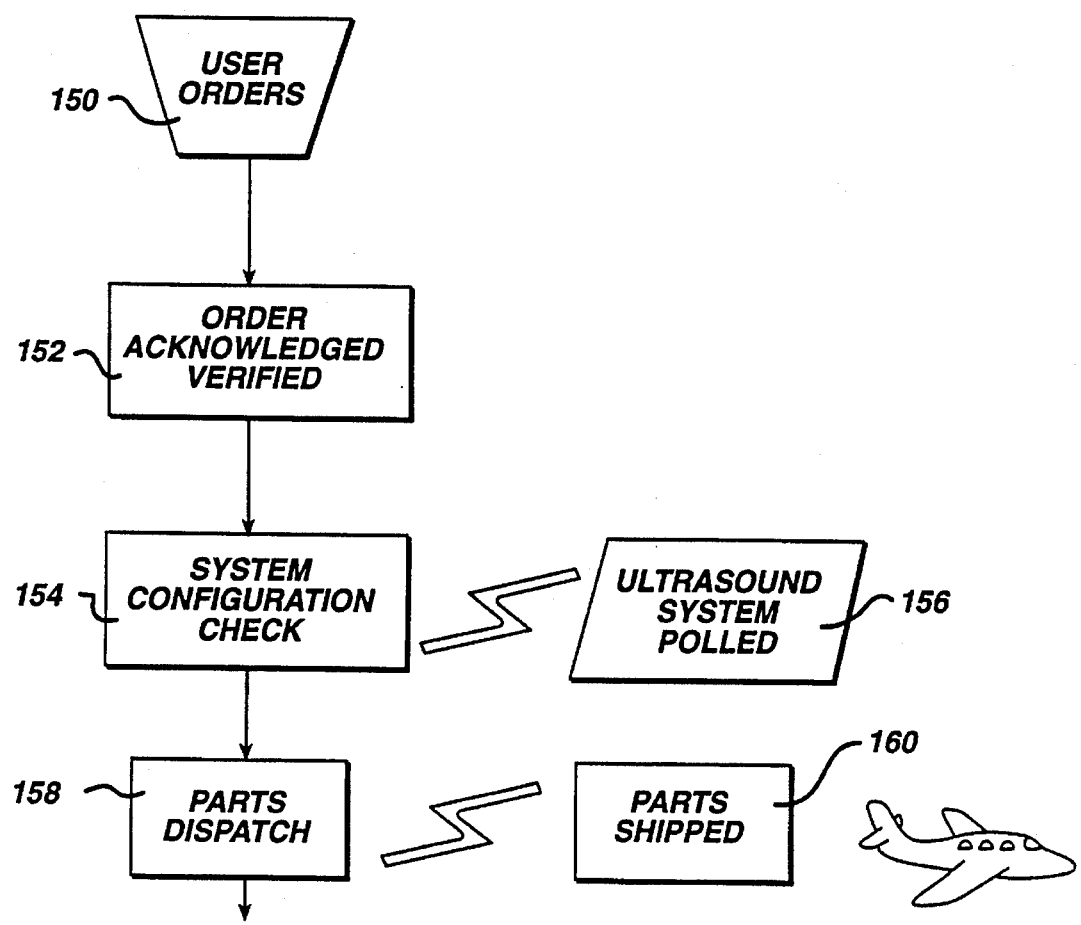
FIGS. 4a and 4b illustrate in flowchart form a process for providing a diagnostic ultrasound system with a transducer probe upgrade in accordance with the principles of the present invention.
Figure 4B:
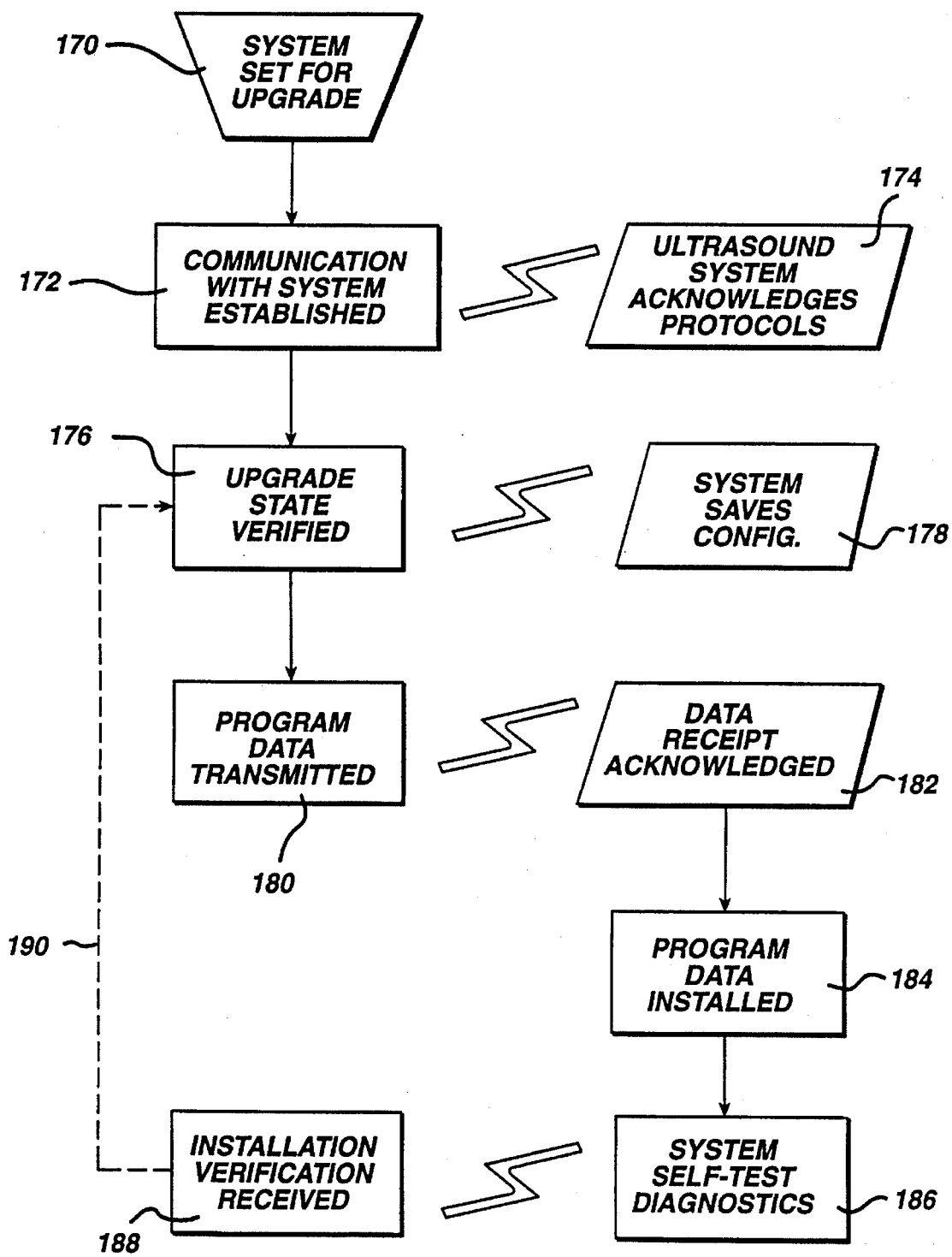

The following example, illustrated with reference to the flowcharts of FIGS. 4a and 4b, shows how an upgrade including both hardware and program data components is remotely installed in the ultrasound system 100 in accordance with the process of the present invention. The subject of this example is a scanhead upgrade, by which the ultrasound system is provided with a new scanhead and the program data required by the ultrasound system to operate and control the scanhead. For purposes of the example it will be assumed that the physician who uses the ultrasound system desires to perform an ultrasound exam the following day, for which he needs a scanhead he does not presently have and which cannot presently operate with his ultrasound system.

In this situation the physician picks up the telephone and calls the factory. His call is answered by a service representative, with whom the physician places an order for a new broadband, curved array scanhead called (in this scenario) a C8-3 scanhead. This is the first step 150 in the flowchart of FIG. 4a. At step 152 the physician's order is acknowledged and verified to ascertain that a C8-3 scanhead is an upgrade which can be added to the physician's ultrasound system.

The service representative then begins the process which will culminate in the delivery and installation of the C8-3 scanhead upgrade for the physician. The first step in the process, at 154, is to check the configuration of the physician's system. This involves checking the version, or level, of the operating software of the system, and the hardware components of the ultrasound system. The current configuration of the physician's ultrasound system will establish the additional hardware and/or program data which is needed to add the upgrade to the physician's ultrasound system, component which are both compatible and effective with this system. The necessary information is generally available in two ways. One is a database maintained by the factory of the current configurations of all ultrasound systems sold by the manufacturer. The weakness of this system is that it is dependent upon timely and accurate updates as the configuration of the system is changed. If the configuration is changed by third parties who do not provide the new configuration information to the database, the database will be in error. This deficiency is overcome by the second method of ascertaining the configuration, which is to poll the ultrasound system from the factory by way of the communications medium and the system's communications link. The service representative will establish communication with the physician's ultrasound system and send a command to the system, requesting that the ultrasound system transmit its configuration information to the factory. The communications link, under control of the processor, responds to this inquiry by sending the current configuration information over the communications medium and back to the service representative at the factory, as indicated at 156. Thus, the service representative is able to accurately determine the current configuration of the ultrasound system remotely, without a service call to the physician's laboratory and without inconveniencing the physician.

The latter alternative raises important issues when technology is applied to the practice of medicine, the issues of patient privacy and diagnostic security. Since virtually all of the components and programs of the ultrasound system are interrelated and interactive, the ability to remotely poll an ultrasound system for its configuration information implies (correctly or not) that remote polling can access other information resident within the machine, such as patient data and diagnostic report data. Regardless of whether such capabilities can be realized, the physician must be assured that the ultrasound system will meet the levels of privacy and security he demands and the law requires, and that he controls such privacy and security.

The success of such assurances begins at the time the ultrasound system is first installed in the physician's laboratory. At that time, the factory installation personnel explain the remote polling capabilities of the ultrasound system to the physician and allow him to select the level of remote polling of which his system will be capable. The physician may elect that his ultrasound system be set up to permit only configuration polling, with access to all other information in the machine being inhibited or locked out. Alternatively, the physician may permit greater remote access, such as access to ultrasound system diagnostic and performance information. Or, the physician may permit access to some patient data such as image data. Of course, the physician will always have the option of blocking, or locking out, access to all remote polling of the ultrasound system's information. The balance between privacy and security on the one hand, and faster, more accurate diagnostic support from the factory on the other, will be one which is struck by the physician.

Once the configuration of the ultrasound system has been ascertained, the service representative dispatches the proper hardware components of the upgrade to the physician's site in step 158. The hardware components for upgrades are preferably stocked at a location from which they can be promptly shipped to customers. ATL (Advanced Technology Laboratories, Inc.), the assignee of the present application, stocks upgrade components, not at ATL's factory, but at the facilities of an air freight shipping company. To dispatch a component the service representative either calls or contacts the shipper electronically, giving instructions for the part to be shipped and its destination. The shipping company immediately dispatches the component from its facility and the part is shipped by air for delivery to the customer the following morning, or earlier if circumstances so require, as indicated at 160 of FIG. 4a.

At step 170 the physician sets the ultrasound system in an operating state to receive the upgrade program data which will be transmitted to the system by the factory. It may be that, at the time the physician places the upgrade order, he intends to continue to use the system for patient examinations for the rest of the day. The ultrasound system cannot be upgraded while it is in diagnostic use, and indeed care must be taken to avoid doing so, in order that the physician's patient exams not be interrupted. Hence, the physician will not set the system in a state to receive the upgrade program data until it is convenient for his purposes. This may be at the end of the physician's appointment day, for instance, when the ultrasound system would otherwise be idle. The physician will be asked to indicate a convenient time for the upgrade to be installed at the time he places the order. In a typical embodiment, setting the ultrasound system in a state to receive the upgrade simply means leaving the system powered up, the communications link 60 turned on, and the communications cable connected to the local network port or telephone line 104. The ultrasound system will preferably be equipped with a single hard or softkey button labeled "Receive Upgrade Data" which, when depressed, will condition the electronic elements of the ultrasound machine to receive upgrade program data over the communications media.

At step 172 the service representative establishes communication with the ultrasound system 100 over the communications media from the program data server 120. The ultrasound system is password protected and requires the exchange and acknowledgment of predetermined protocols before communication with the ultrasound system is established at step 174. After communication between the program data server and the ultrasound system has been established, the server will request and receive verification from the ultrasound system that the system is in a state in which the upgrade program data can be received and installed. The service representative will then communicate to the ultrasound system that the server is ready to begin transmission of upgrade program data.

At step 178 the ultrasound system saves its current configuration data, if it has not previously done so. This configuration data includes not only presets and default parameters that were installed previously by the factory, such as "Tissue Specific Imaging" parameters which automatically enable the ultrasound system to conduct certain diagnostic examinations, but also custom presets and parameters which the user has added to the system. The physician may have set parameters and presets into the ultrasound system which cause the system to operate to his personal requirements. As an example, the physician may have preset a linear array probe to automatically have a certain set of transmit focal points each time the probe is used, avoiding the need for the physician to manually set the focal points before each examination. This customized information is stored by the ultrasound system at step 178, so that it will not be lost and can be reinstalled at the conclusion of upgrade program data installation.

With the ultrasound system in a state to receive upgrade program data and the configuration information saved, at step 180 the program data server 120 begins the transmission of the upgrade program data to the ultrasound system by way of the communications media. The communications link 60 receives the program data and after the complete data set has been received, the communications link at step 182 acknowledges receipt of the data. The transmitted data may, in addition to the program data required for the upgrade, include diagnostic self-test routines for the ultrasound system to use to verify successful installation of the upgrade.

At step 184 the ultrasound system processor installs the program data in the system. This step may include preparatory steps such as decompressing data which was sent in compacted form, and/or preparing and ordering subsets of the data for installation and storage in different subsystems within the ultrasound system. In the instance of the scanhead upgrade of the present example, the upgrade program data would include tabular data and instructions enabling the beamformer to energize the transducer elements of the new scanhead at proper times, to properly delay received ultrasound signals to form a correctly focused and steered beam, and to provide user control settings by which the physician can control the power output level of the probe, among other things. Data subsets appropriate for these functions and others are processed as necessary by the processor and stored in the appropriate storage media of the ultrasound system.

After the upgrade program data has been installed, the ultrasound system tests and checks elements of the system to verify proper installation of the program data and performs the self-test diagnostics which may have been transmitted with the upgrade data as indicated at step 186. The results of these checks and test, such as memory check-sum results and configuration test results, are transmitted back to the program data server at step 188 to verify proper installation of the upgrade program data. During the course of the installation and verification procedures, the ultrasound system will reinstall the customized configuration settings which were saved earlier.

If for some reason complete verification of a successful upgrade installation is not received by the server, the service representative will query the ultrasound system for information which may reveal the source of any difficulty, and proceed to resolve it. If necessary, the process can return to step 176, as indicated by dashed line 190, and reexecute the entire upgrade process.

It is seen that the upgrade program data is installed in the ultrasound system from a remote location, without the need for intervention by the physician or service personnel at the site of the ultrasound system. The upgrade can be performed during a time when the ultrasound system is not in service, such as during late night hours at the system site. Since the remote location of the server 120 can be anywhere on the globe, the upgrade can be installed during working hours at the server site, but during off-hours at the ultrasound system site. Ultrasound systems in Europe can be upgraded in the middle of the night, local time, and during normal working hours of the server site in Seattle, for example.

Under the scenario of the present example, the upgrade program data is transmitted, received and installed in the physician's ultrasound system overnight. The scanhead arrives the following morning from the air freight delivery service. The physician plugs the scanhead into a connector 80 and is able at once to proceed to conduct diagnostic examinations with the new scanhead and upgraded ultrasound system.

Figure 5:
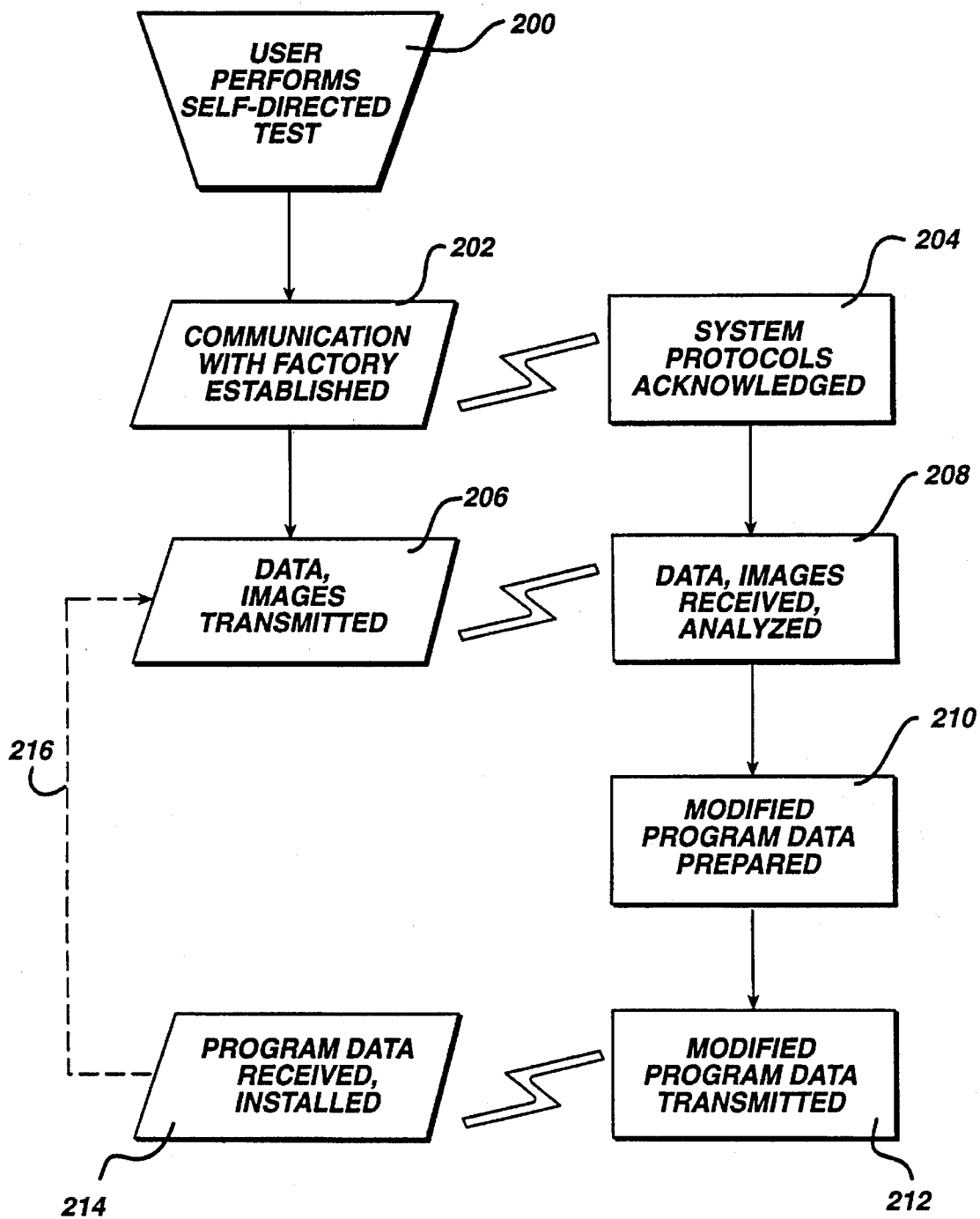
FIG. 5 illustrates in flowchart form a process for remotely providing diagnostic support for a diagnostic ultrasound system.

As an optional adjunct to the remote transmission and installation of upgrades, FIG. 5 illustrates a process by which performance of the ultrasound system upgrade can be further verified by the physician and any needed adjustments or refinements made. In step 200 the physician performs a self-directed test of his new scanhead. This test may involve use of some of the self-test diagnostics which were transmitted to the ultrasound system during the installation process. In the case of a scanhead upgrade, it can also include activities such as imaging an ultrasound phantom, or imaging normal pathology. These tests, in any event, are specially designed to be easily carried out by the physician himself.

If the physician is dissatisfied with the results of the self-directed testing he can call the factory as shown in step 202, which responds in step 204 by establishing communication with the ultrasound system by the exchange of passwords and protocols as discussed above. With the factory now in communication with the ultrasound system in the presence of the physician, the physician and the factory service representative can discuss any problems and jointly determine how to proceed to resolve any problems. In step 206, for instance, the physician and service representative decide to provide system data and ultrasound images from the ultrasound system for analysis by the factory. This information is received by the factory over the communication media in step 208, where a specialist analyzes the information and images. In step 210, for instance, the factory specialist determines that a modification to the upgrade program data is appropriate, and a modified program data set is prepared. This modified program data set is transmitted over the communications media by the server 120 in step 212, where it is received in step 214 by the ultrasound system and installed. The physician can then test the upgrade feature with the newly installed data set and, as dashed line 216 indicates, the transmission of ultrasound system information and return of modified program data can continue until the physician is fully satisfied with the upgrade performance.

From the above description, other applications of the present invention will be readily apparent to those skilled in the art. For instance, many upgrades can be encompassed entirely within a program data set, with no hardware component. Such upgrades are installed from the remote location by means of the communications media, with no need for delivery of hardware. These upgrades can be listed and described on a database readily accessible to many ultrasound system users, such as the World Wide Web homepage of the inventors' assignee company. A user accessing the homepage can order remotely installed upgrades from the homepage and its hypertext links simply by "pointing and clicking" a computer mouse and providing basic ordering information in response to queries to which the user is directed by the homepage. The user can thus place orders for upgrades at his convenience, which are immediately communicated to service representatives for remote installation at the time desired by the user. The homepage hypertext links also enable a user communicating with the homepage through his ultrasound system and communications link to receive program data upgrades immediately by means of the homepage and/or its hypertext links.

It will also be appreciated that upgrade program data can be transmitted to the ultrasound system even at times when the system is in diagnostic use by providing a buffer, or data storage, where incoming program data can be temporarily stored for later installation. Such a buffer allows the service representative to transmit upgrade program data at any time without waiting for the ultrasound system to be set in a state for upgrade installation. When the system is later set in the "upgrade installation" state, the buffered program data is accessed, processed and installed in the ultrasound system. At the conclusion of the upgrade installation the communications link establishes communication with the server at the factory, and the system reports the status and success of the upgrade installation.

It will also be appreciated that the ultrasound system with its upgrade communications link can be operated at remote locations even where telephone lines are not accessible. A modem of the system can be connected to a cellular telephone, for instance, enabling the reception and installation of upgrade data whenever the ultrasound system is within range of a cellular telephone service area.

What is claimed is:

1. A process for providing scanhead upgrades to a remotely upgradeable medical diagnostic ultrasound system which includes a communications link for establishing a data link over a common carrier communications network between said ultrasound system and a remote factory location comprising the steps of:

receiving an order from a customer for a scanhead upgrade;

checking the configuration of the ultrasound system which is to receive the scanhead upgrade;

dispatching a scanhead by air to the location of the ultrasound system;

establishing a data communications link over a common carrier communications network between a program data server at the factory and the ultrasound system;

transmitting upgrade program data from the program data server to the ultrasound system over the data communications link;

receiving the upgrade program data by the ultrasound system;

installing the upgrade program data in the ultrasound system; and reporting by the ultrasound system to the program data server that the upgrade program data has been successfully received or installed.

2. The process of claim 1, wherein the step of checking the configuration of the ultrasound system comprises the step of establishing a data communications link over a common carrier communications network between a program data server at the factory and the ultrasound system; and acquiring configuration data of said ultrasound system over said communications network by said program data server.

3. The process of claim 1, wherein the step of installing the upgrade program data in the ultrasound system is performed subsequent to ending the communications link between said server and said ultrasound system during which said upgrade program data was received.

4. The process of claim 1, further comprising the step of verifying successful installation of the upgrade program data by performing a diagnostic test at said ultrasound system.

5. The process of claim 4, wherein the step of transmitting upgrade program data further comprises the step of transmitting diagnostic test data for said upgrade.

6. The process of claim 4, wherein the step of verifying successful installation of the upgrade program data comprises the performance of a self-directed test by an ultrasound system user.

7. The process of claim 6, further comprising the step of transmitting diagnostic information concerning said upgrade to a program data server for remote analysis of the performance of the upgrade.

8. The process of claim 7, further comprising the step of transmitting modifying upgrade program data to said ultrasound system.

9. The process of claim 7, wherein said diagnostic information comprises ultrasound image data.

10. The process of claim 1, wherein the step of transmitting upgrade program data comprises transmitting data to said ultrasound system which is used by said ultrasound system to control or process signals transmitted between said scanhead and said ultrasound system during use of said scanhead.

11. A medical diagnostic ultrasound system which is capable of being upgraded by the addition of new or different performance features and functions, including means for remotely upgrading said ultrasound system comprising:

a communications link, coupled to a data bus of said ultrasound system, and controlled by said ultrasound system to receive ultrasound upgrade program data transmitted from a remote location over a common carrier communications medium; and a processor for installing said ultrasound upgrade program data in said ultrasound system following its receipt by said ultrasound system, said upgrade program data providing some or all of the functionality of an ultrasound system upgrade.

12. The medical diagnostic ultrasound system of claim 11, wherein said communications link comprises a network data link.

13. The medical diagnostic ultrasound system of claim 11, wherein said communications link comprises a modem.

14. The medical diagnostic ultrasound system of claim 11, further comprising a data storage device coupled to said data bus for storing upgrade program data received by said communications link for upgrading said ultrasound system.

15. The medical diagnostic ultrasound system of claim 14, wherein said processor is coupled to said data storage device for installing upgrade program data received by said communications link in said ultrasound system.

16. The medical diagnostic ultrasound system of claim 11, wherein said communications link includes means for acknowledging communications contact from a remote location for receiving upgrade program data from said server.

17. The medical diagnostic ultrasound system of claim 16, wherein said communications link includes means for communicating with said remote location after receiving upgrade program data from said location for acknowledging the successful receipt of upgrade program data.

18. A medical diagnostic ultrasound system which is capable of being remotely polled to determine its current configuration comprising:

a data storage device which stores digital data comprising configuration information of said ultrasound system; and a communications link, coupled by means of a data bus of said ultrasound system to said data storage device, and responsive to an electronic request from a remotely located terminal for transmitting said configuration information over a common carrier communication medium to said terminal location.

19. The medical diagnostic ultrasound system of claim 18, wherein said communications link comprises a network data link.

20. The medical diagnostic ultrasound system of claim 18, wherein said communications link comprises a modem.

21. The medical diagnostic ultrasound system of claim 18, further comprising a remote access controller, controllable by said user, to permit or block access by a remote terminal to said configuration information.

22. The medical diagnostic ultrasound system of claim 21, wherein said remote access controller is further controllable by said user to permit or block access by a remote terminal to other information stored by said ultrasound system in addition to said configuration information.

23. A medical diagnostic ultrasound system which is capable of being remotely polled to provide information concerning said ultrasound system to a remote location comprising:

a data storage device which stores digital data comprising patient data and/or information concerning operating characteristics of said system;

a communications link, coupled by means of a data bus of said ultrasound system to said data storage device, and responsive to an electronic request from a remotely located terminal for transmitting digital data from said system over a common carrier communication medium to said terminal location; and a security device which is controllable by a user of said ultrasound system to preclude said communications link from transmitting digital data of a predetermined character to said remote location.

24. The medical diagnostic ultrasound system of claim 23, wherein said communications link comprises a network data link.

25. The medical diagnostic ultrasound system of claim 23, wherein said communications link comprises a modem.

26. The medical diagnostic ultrasound system of claim 23, wherein said security device is controllable by said user to permit or block access by a remote terminal to configuration information of said ultrasound system stored by said ultrasound system.

27. The medical diagnostic ultrasound system of claim 26, wherein said security device is further controllable by said user to permit or block access by a remote terminal to patient information stored by said ultrasound system in addition to said configuration information.

28. A process for providing program data upgrades to a remotely upgradeable medical diagnostic ultrasound system which includes a data communicator for establishing a data link over a common carrier communications network between said ultrasound system and a remote program data server comprising the steps of:

receiving an order from a customer for an ultrasound upgrade;

checking the configuration of the ultrasound system which is to receive the ultrasound upgrade;

establishing a data communications link over a common carrier communications network between the data communicator of said ultrasound system and the remote program data server;

transmitting upgrade program data from the program data server to the ultrasound system;

receiving the upgrade program data by the data communicator in the ultrasound system; and installing the upgrade program data in the ultrasound system.

29. The process of claim 28, wherein the step of checking the configuration of the ultrasound system comprises the steps of establishing a data communications link over a common carrier communications network between a program data server at the factory and the ultrasound system; and acquiring configuration data of said ultrasound system from the data communicator over said communications network by said program data server.

30. The process of claim 28, wherein the step of installing the upgrade program data in the ultrasound system is performed subsequent to ending the communications link between said server and said ultrasound system during which said upgrade program data was received.

31. The process of claim 28, further comprising the step of verifying successful installation of the upgrade program data by performing a diagnostic test at said ultrasound system.

32. The process of claim 31, wherein the step of transmitting upgrade program data further comprises the step of transmitting diagnostic test data for said upgrade.

33. The process of claim 31, wherein the step of verifying successful installation of the upgrade program data comprises the performance of a self-directed test by an ultrasound system user.

34. The process of claim 33, further comprising the step of transmitting diagnostic information concerning said upgrade to a program data server for remote analysis of the performance of the upgrade.

35. The process of claim 34, further comprising the step of transmitting modifying upgrade program data to said ultrasound system.

36. The process of claim 34, wherein said diagnostic information comprises ultrasound image data.

37. The process of claim 28, wherein the step of transmitting upgrade program data comprises transmitting data to said ultrasound system which is used by said ultrasound system to control or process ultrasonic patient information for display by said ultrasound system.

* * * * *